US012766109B2

(12) United States Patent
Kempa et al.

(10) Patent No.: US 12,766,109 B2
(45) Date of Patent: Oct. 20, 2026

(54) SUGAR-COATED MELANIN NANOPARTICLES AND METHOD FOR TARGETING METASTATIC CANCER CELLS

(71) Applicants: Krzysztof Kempa, Chestnut Hill, MA (US); Michael J Naughton, Waltham, MA (US)

(72) Inventors: Krzysztof Kempa, Chestnut Hill, MA (US); Michael J Naughton, Waltham, MA (US)

(73) Assignee: The Trustees of Boston College, Chestnut Hill, MA (US)

( * ) Notice: Subject to any disclaimer, the term of this patent is extended or adjusted under 35 U.S.C. 154(b) by 646 days.

(21) Appl. No.: 18/122,221

(22) Filed: Mar. 16, 2023

(65) Prior Publication Data

US 2023/0293441 A1 Sep. 21, 2023

Related U.S. Application Data

(60) Provisional application No. 63/320,403, filed on Mar. 16, 2022.

(51) Int. Cl.
*A61K 9/20* (2006.01)
*A61K 9/00* (2006.01)
*B82Y 5/00* (2011.01)

(52) U.S. Cl.
CPC .......... *A61K 9/2031* (2013.01); *A61K 9/0019* (2013.01); *B82Y 5/00* (2013.01)

(58) Field of Classification Search
None
See application file for complete search history.

(56) References Cited

U.S. PATENT DOCUMENTS

2020/0085931 A1 * 3/2020 Wang ............. A61K 39/001188
2020/0113934 A1 * 4/2020 Gianneschi .......... A61K 9/0019

OTHER PUBLICATIONS

Antonella De Trizio et al. "Natural based eumelanin nanoparticles functionalization and preliminary evaluation as carrier for gentamicin." Reactive and Functional Polymers, vol. 114, 2017, pp. 38-48. (Year: 2017).*
Mario Moros et al. "Monosaccharides versus PEG-Functionalized NPs: Influence in the Cellular Uptake." ACS Nano, vol. 6 No. 2, 2012, pp. 1565-1577 and 17 pages of supplemental information. (Year: 2012).*
Bionumbers. "Size of glucose molecule." https://bionumbers.hms.harvard.edu/bionumber.aspx?id=106979&ver=1 accessed Jun. 9, 2025. (Year: 2025).*
Lei Rong et al. "Iron chelated melanin-like nanoparticles for tumor-associated macrophage repolarization and cancer therapy." Biomaterials, 225 (2019) 119515, pp. 1-9. (Year: 2019).*
Bionumbers. "Size of Glucose Molecule." https://bionumbers.hms.harvard.edu/bionumber.aspx?id=106979&ver=1 accessed Jun. 9, 2025, 1 page. (Year: 2025).*

(Continued)

*Primary Examiner* — Isaac Shomer
(74) *Attorney, Agent, or Firm* — Bond Schoeneck & King, PLLC; Joseph M. Noto

(57) ABSTRACT

Disclosed is a method for the cellular uptake of sugar-coated melanin nanoparticles by metastatic cancer cells followed by illumination with nonionizing radiation (e.g., visible or IR light) causing cell death.

9 Claims, 9 Drawing Sheets

(56) References Cited

OTHER PUBLICATIONS

University of Muenchen. "Amino acids and their Abbreviations." https://www.cup.uni-muenchen.de/ch/compchem/tink/as.html accessed on Feb. 18, 2026, 3 printed pages. (Year: 2026).*
Victoria R. Gabriele et al. "Light- and Melanin Nanoparticle-Induced Cytotoxicity in Metastatic Cancer Cells." Pharmaceutics, 2021, 13, 965, pp. 1-13. (Year: 2021).*
Stefania Cuzzubbo et al. "Applications of Melanin and Melanin-Like Nanoparticles in Cancer Therapy: A Review of Recent Advances." Cancers, 2021, 13, 1463, pp. 1-15. (Year: 2021).*
Yinping Li et al. "Photothermally triggered cytosolic drug delivery of glucose functionalized polydopamine nanoparticles in response to tumor microenvironment for the GLUT1-targeting chemo-phototherapy." Journal of Controlled Release, vol. 317 (2020), pp. 232-245. (Year: 2020).*
Maria Moros et al. "Monosaccharides versus PEG-Functionalized NPs: Influence in the Cellular Uptake." ACS Nano, vol. 6 No. 2, 2012, pp. 1565-1577 and 16 pages of supplemental information. (Year: 2012).*

* cited by examiner

1 µm

1 µm 800 nm 500 nm 500 nm y = −173 x + 1904
R² = 0.97
size (nm)
pH
0
100
200
300
9
9.5
10
10.5 experiment
$P/P_{max}$
$x$ (μm)

10 μm $t$ = 0 sec $t$ =15 sec $t$ =30 sec

10 μm
$t$ = 0 sec $t$ = 0.1 sec $t$ = 3 sec before
after
number of cells
0
20
40
60
80
100
1
2
3
4
5

FIG. 9A
FIG. 9B
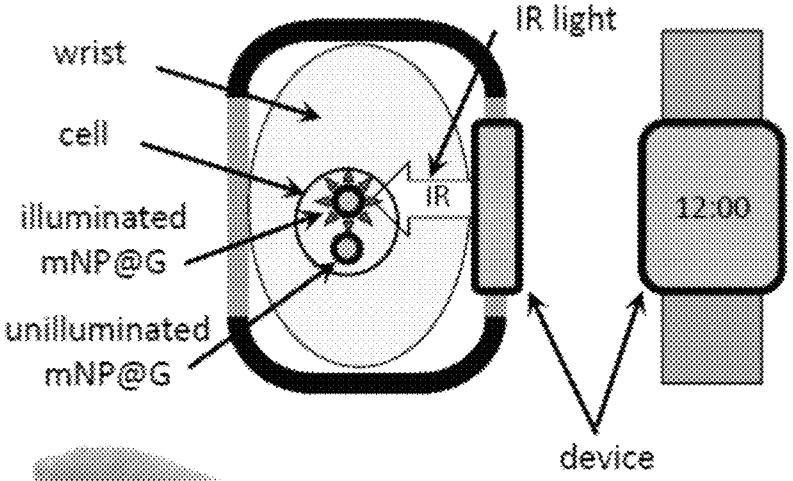
FIG. 9C
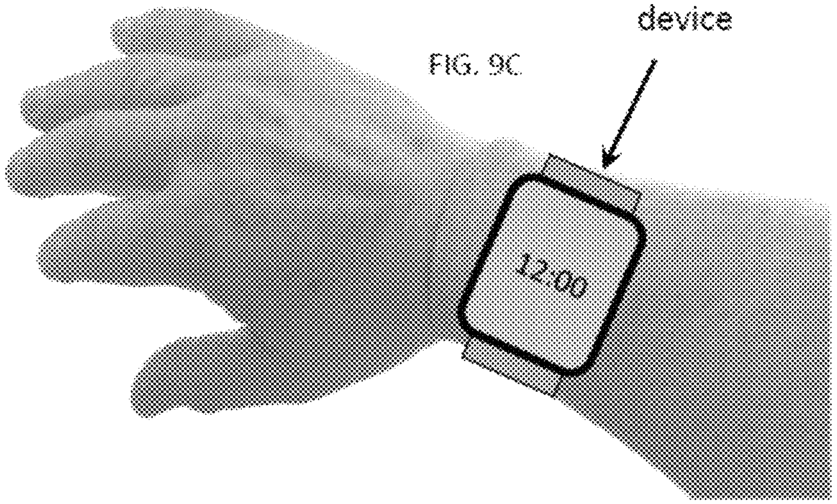

SUGAR-COATED MELANIN NANOPARTICLES AND METHOD FOR TARGETING METASTATIC CANCER CELLS

CROSS REFERENCE

This application claims the benefit of the filing date of U.S. Provisional Patent Application No. 63/320,403, filed Mar. 16, 2022, which is hereby incorporated by reference in its entirety.

This invention was made with government support under grant number PHY1748906 awarded by the National Science Foundation. The government has certain rights in the invention.

FIELD

The present invention relates to a method for the cellular uptake of sugar-coated melanin nanoparticles by metastatic cancer cells followed by illumination with nonionizing radiation causing cell death.

BACKGROUND

The emergence of nanoparticle (NP) technology in biomedicine has led to many applications. These include tumor imaging and targeting, tissue engineering, drug delivery, tumor destruction, pathogen detection, and protein detection, among others. Sufficiently small nonpolar NPs can cross biological barriers and translocate across cells, tissues, and organs. In contrast, polar NPs can enter cells only by utilizing endocytotic pathways. The internalization process of NPs by cells is a key factor in determining their biomedical function, toxicity, and biodistribution. Adjusting chemophysical properties of NPs, such as size, shape, and surface properties, is a major factor for optimization of targeting and cellular uptake, as well as intracellular trafficking. Zeta potential (ξ) could be an important biophysical parameter for quantification of the cellular interactions.

Meanwhile, it has been also known for over a century that biomolecules can be irreversibly damaged by ionizing radiation, via photons with energy sufficient to break covalent bonds. For example, ultraviolet (UV) radiation is known to cause catastrophic damage to cells, and X-rays and even harder radiation have been long applied to treat cancer. Such radiation damages of cells and tissue is largely indiscriminate, with minimal or no spectral control or biospecificity. Therefore, geometric targeting must be used to achieve some degree of macro-scale selectivity. Non-ionizing radiation, with photons of much lower energy can, at sufficient intensity, also cause irreversible damage to biomolecules via non-linear processes (under high local electric or thermal field). Geometric targeting can be improved with such radiation due to the availability of lensing, in particular in the visible frequency range. Irreversible damage of geometrically microtargeted yeast cells was recently demonstrated, using laser tweezers employing a low power (80 mW), near infrared (NIR) laser focused to a spot of about 1 μm diameter (~$10^{10}$ W/$m^2$). Most importantly, however, nonlinear effects produced by non-ionizing radiation allow for spectral resolution of the excitation. Spectra in the NIR and far IR (FIR) ranges consist typically of characteristic groups of absorbance maxima, which form so called "fingerprint" spectra, and which can be used to identify a given molecule. A recent theoretical paper suggested that such fingerprint spectra can be used to selectively damage target molecules within a cell. Such purely spectral selectivity of molecular dissociation would be highly desirable in future therapies, but it is currently very hard (or impossible) to achieve/implement, mainly because the spectra of different biomolecules (ranging from viral to cellular, healthy or cancerous) are very similar, typically with only some amplitude variations, but at similar or the same peak spectral locations (wavelengths). An additional complication is the generally small radiation penetration depth, apart from a few high transparency spectral windows.

These technical difficulties can be overcome with the incorporation of strongly light-absorbing targets, such as NPs. For example, light absorption by melanin NPs is very strong (typically an order of magnitude more than typical cells) over a wide spectral range, a fact that has been exploited in the detection of metastatic melanoma circulating tumor cells (CTC). Several papers have shown that, for wavelengths around 500 nm and between 700 nm and 900 nm, melanoma cells dominate absorption over that of blood, suggesting they may be able to be overheated with radiation at those wavelengths. In fact, RBC-M hybrid membrane-coated melanin NPs have been used recently to trigger cell death by over-heating (over 42° C.) in tumors. In such tumor therapy, radiation in the NIR high transparency window (~800 nm wavelength) is typically used.

While melanin, the pigment present in abundance in melanoma cells, plays an important role in skin protection against ultraviolet radiation, it also affects melanoma behavior by adjusting epidermal homeostasis. Melanoma is, of course, a serious skin cancer, originating from mutated melanocytes, melanin-producing cells. Highly metastatic, it causes about 60,000 deaths per year globally. Very limited progress treating melanoma has been achieved with chemotherapy, immunotherapy, radiotherapy, surgery, or other therapies. Melanin synthesis, a multistep and highly regulated route, determines the difference between the function of normal and cancerous cells. Different from healthy melanocytes, in which melanin synthesis is controlled by various factors and plays an important biological role, melanin pigmentation in melanoma cells is dysregulated, which leads to heavy pigmentation of these cells. Sarna et al. have suggested that the elastic properties of melanoma cells are affected by the melanin presence and play a key role in melanoma metastasis. Other studies confirm that melanin pigmentation is an important factor in determining the fate of cancer cells. Metabolic functions of normal cells are dramatically changed in the cancerous state, and this transformation makes cancer cells strongly dependent on high rates of glucose uptake.

To achieve rapid cancer cell proliferation in vitro, cell culturing methods commonly use high glucose of Dulbecco's modified Eagle's medium (DMEM, 25 mM or 4500 μg $mL^{-1}$). Normal serum glucose levels in the body are usually constant between 4 and 6 mM (720-1,080 μg $mL^{-1}$). However, the body may experience a drop in glucose level to 2.5 mM (450 μg $mL^{-1}$), and even further in tissue, in the case of nutrient deficiencies. Accordingly, glucose level reduction has been applied for cancer treatment through different methods such as fasting or modifying (e.g., ketogenic) diet.

SUMMARY

In accordance with one aspect of the present invention, there is provided a method for treating metastatic cancer cells, including coating melanin nanoparticles with sugar; exposing metastatic cancer cells to the sugar-coated melanin nanoparticles causing nanoparticle uptake at a nanoparticle density to sensitize the cancer cells; and illuminating the sensitized cancer cells with a power level of nonionizing radiation sufficient to cause cell death.

These and other aspects of the present disclosure will become apparent upon a review of the following detailed description and the claims appended thereto.

BRIEF DESCRIPTION OF THE DRAWINGS

FIG. 9A is a cross-section of a side-view of the wrist device worn on the arm of a user, FIG. 9B is a top view of the device, and FIG. 9C is a sketch of the device worn on a human wrist.

DETAILED DESCRIPTION

Figures 1A, 1B, 1C, 1D, 1E, 1F:
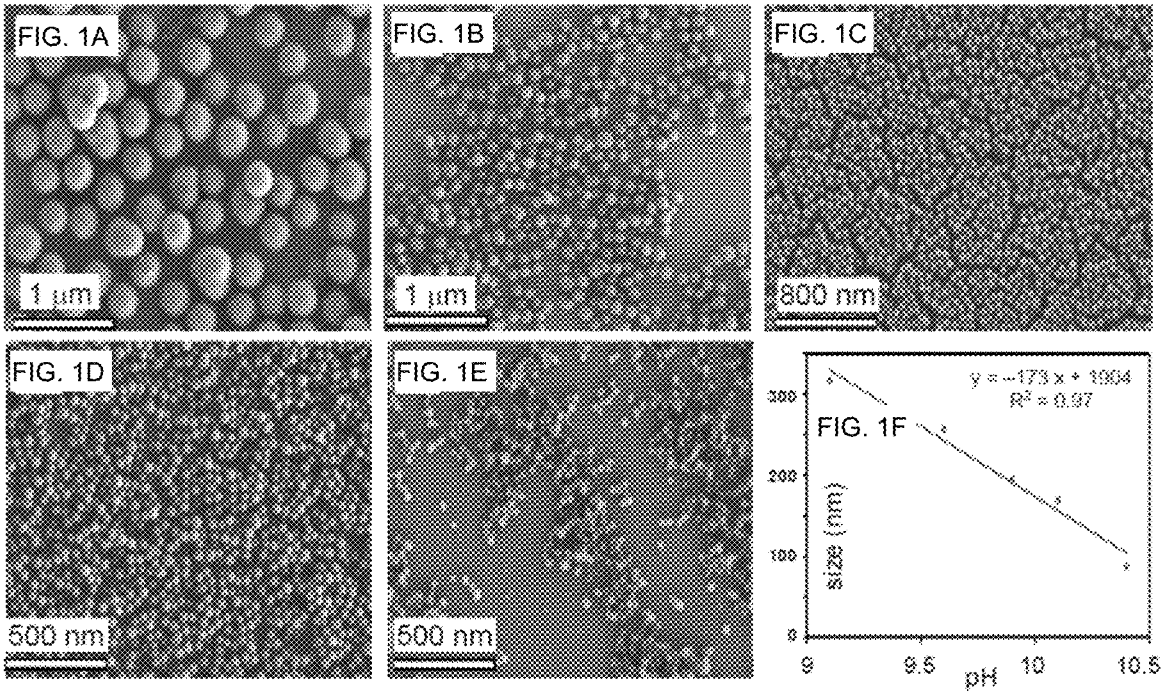
FIG. 1A is an SEM image of mNPs in 0.5 mL of $NH_4OH$, FIG. 1B in 1.0 mL of $NH_4OH$, FIG. 1C in 1.5 mL of $NH_4OH$, FIG. 1D in 2.0 mL of $NH_4OH$, FIG. 1E in 2.5 mL of $NH_4OH$.
FIG. 1F is a plot of mNP diameter vs. pH of $NH_4OH$ solution.

Disclosed is a massive cellular uptake of melanin nanoparticles by diseased-state biological cells followed by illumination with nonionizing radiation (e.g., visible or IR light) causes cell death. In particular, metastatic cancer cells can be photodynamically killed after melanin nanoparticle uptake plus optical illumination since, at sufficiently high nanoparticle density and light energy, this uptake is cytotoxic. This effect can be further enhanced by coating the melanin nanoparticles with sugar (e.g., glucose) and application of nonionizing radiation (visible or IR). Cell death occurs via hyperthermia-induced lysis.

In an embodiment, a method for treating metastatic cancer cells, includes coating (e.g., about 10 to 30 nm thick) melanin nanoparticles (for example, having a diameter of between 50 and 350 nm) with sugar (e.g., glucose); exposing metastatic cancer cells to the sugar-coated melanin nanoparticles causing nanoparticle uptake at a nanoparticle density to sensitize the cancer cells; and illuminating the sensitized cancer cells with a power level of nonionizing radiation (e.g., visible or IR light) sufficient to cause cell death.

The sugar-coated melanin nanoparticles have a melanin nanoparticle core with a diameter of from between 50 and 350 nm. The sugar-coated melanin nanoparticles have a 10 to 30 nm coating of sugar surrounding the core.

This process is highly target-selective, as healthy cells that do not ingest, or ingest significantly smaller specific volumes of, melanin nanoparticles, remain unaffected, despite receiving identical optical power levels and doses (i.e., frequency and intensity of light).

This invention could be used as a basis for a disease therapy, including cancer, by targeting e.g., circulating tumor cells (CTCs) which mediate metastasis. In such a therapy, an intravenous injection of nanoparticles in solution could accomplish the stage of the nanoparticle feeding into CTCs. Then, in one possible scenario, one could expose the blood of a cancer patient to light externally, in a dialysis-like scheme, or by direct radiation exposure of a near skin blood vessel such as a vein or artery (e.g., in the wrist), using radiation in the nominal 700 to 800 nm wavelength transmission window, which would allow a non-invasive version of this therapy. This proposed cancer therapy via blood treatment could dramatically reduce the chance or effect of metastasis. In an embodiment, FIG. 9A is a cross-section of a side-view of a device worn on the wrist of a user depicting a wrist and a representative CTC containing two representative glucose-coated mNPs, one of which is illuminated by the IR light (and subsequently absorbs the IR light causing heating and cell death), and one of which is unilluminated. FIG. 9B is a top view of the device. FIG. 9C is a picture of a human wrist wearing a specialized watch, e.g., a wrist-borne device, capable to sending IR light into the arm.

In this work, we demonstrate methods for targeting and killing mammalian cancer cells with visible non-ionizing radiation. We find that photothermal efficiency is massively enhanced when cells are sensitized with synthetic melanin nanoparticles, known to be excellent absorbers of light in the ultra-violet (UV), visible (VIS) and near infrared (NIR) frequency ranges. Nanoparticle uptake is highly efficient for malignant cancer cell lines, and this uptake is further enhanced by coating the melanin nanoparticles with sugar. Death of nanoparticle-filled cells occurs primarily by heating. We show that this process of cell elimination is highly target-selective in the presence of non-sensitized cells.

Melanin nanoparticles are known to be biologically benign to human cells for a wide range of concentrations in a high glucose culture nutrition. There is cytotoxic behavior at high nanoparticle and low glucose concentrations, as well as at low nanoparticle concentration under exposure to (nonionizing) visible radiation. Representative cancer cell lines are VM-M3, A375 (derived from melanoma), and HeLa, all known to exhibit strong macrophagic character, i.e., strong nanoparticle uptake through phagocytic ingestion. Other cancer cell lines are suitable, as all cancer cells are strongly macrophagic. It is known that (i) metastatic VM-M3 cancer cells massively ingest melanin nanoparticles (mNPs); (ii) the observed ingestion is enhanced by coating mNPs with glucose; (iii) after a certain level of mNP ingestion, the metastatic cancer cells studied are observed to die-glucose coating appearing to slow that process; (iv) cells that accumulate mNPs are much more susceptible to killing by laser illumination than cells that do not accumulate mNPs; and (v) non-metastatic VM-NM1 cancer cells do not ingest the mNPs and remain unaffected after receiving identical optical energy levels and doses.

Glucose-coated melanin nanoparticles (mNP@G) were used these to reveal massive NP uptake by the three cancer cell lines, VM-M3, A375, and HeLa, which confirm these cell types' macrophagic character. Zeta potential measurements suggest that this character is related to binding and cellular internalization effects. The viability of all studied cells dramatically decreases at a sufficiently high concentration of mNP@G and reduction of the glucose level in the culture nutrition. Radiation experiments on cancer cells moderately filled with mNP@G, using light in the visible transmission window of blood at 532 nm wavelength, demonstrated that there exist power levels and doses of this radiation that violently destroy cancer cells sensitized with mNPs, but that are apparently safe for cells unsensitized with mNPs.

The disclosure will be further illustrated with reference to the following specific examples. It is understood that these examples are given by way of illustration and are not meant to limit the disclosure or the claims to follow.

EXAMPLES

Reagents—Chemicals are routinely available from commercial sources with high purity. Malignant melanoma A375 and HeLa cell lines can be obtained from the Shanghai Institute of Cell Biology (Shanghai, China).

Synthesis of Melanin Nanoparticles, mNP—The synthesis of highly spherical monodispersed mNPs can be accomplished using the oxidative polymerization of dopamine hydrochloride in the presence of ethanol and ammonia solution at room temperature. Different sizes of nominally spherical nanoparticles can be thus obtained by varying the volume of ammonium hydroxide.

Preparation of an acetylglucose-Coated Melanin Nanoparticles, mNP@G—As-prepared mNPs (20 mg) dissolved in tris-buffer (0.01 M, pH 7.5) followed by addition of 0.5 g acetylglucosamine sugar yields mNP@G.

Cell Viability Measurements—Cell Counting Kit-8 assay (CCK-8, Sigma-Aldrich, St. Louis, MO, USA) can be used to monitor cell viability.

Biocompatibility and Cytotoxicity Measurements—Biocompatibility and cytotoxicity of various concentrations of mNPs and mNP@G from 140 to 2,100 μg $mL^{-1}$ demonstrate cell viability and proliferation of the A375 and HeLa cell lines, with the latter also studied in high (4500 mg $L^{-1}$) and low glucose (1000 mg $L^{-1}$) growth media, using CCK-8 assays. UV-Vis spectrophotometry can be used to evaluate cell viability, cell membrane damage and cell toxicity.

Characterization of mNP@G

FIG. 1 shows SEM images of as-prepared mNPs of different sizes (between 100 and 300 nm), obtained by variation of the $NH_4OH$ solution volume. FIG. 1A is an SEM image of mNPs in 0.5 mL of $NH_4OH$, FIG. 1B is an SEM image of mNPs in 1.0 mL of $NH_4OH$, FIG. 1C is an SEM image of mNPs in 1.5 mL of $NH_4OH$, FIG. 1D is an SEM image of mNPs in 2.0 mL of $NH_4OH$, FIG. 1E is an SEM image of mNPs in 5.5 mL of $NH_4OH$, and FIG. 1F is a plot of mNP diameter vs. pH of $NH_4OH$ solution. As seen in FIG. 1F, the mNP diameter is a linear function of the solution pH.

Figures 2A, 2B, 2C, 2D:
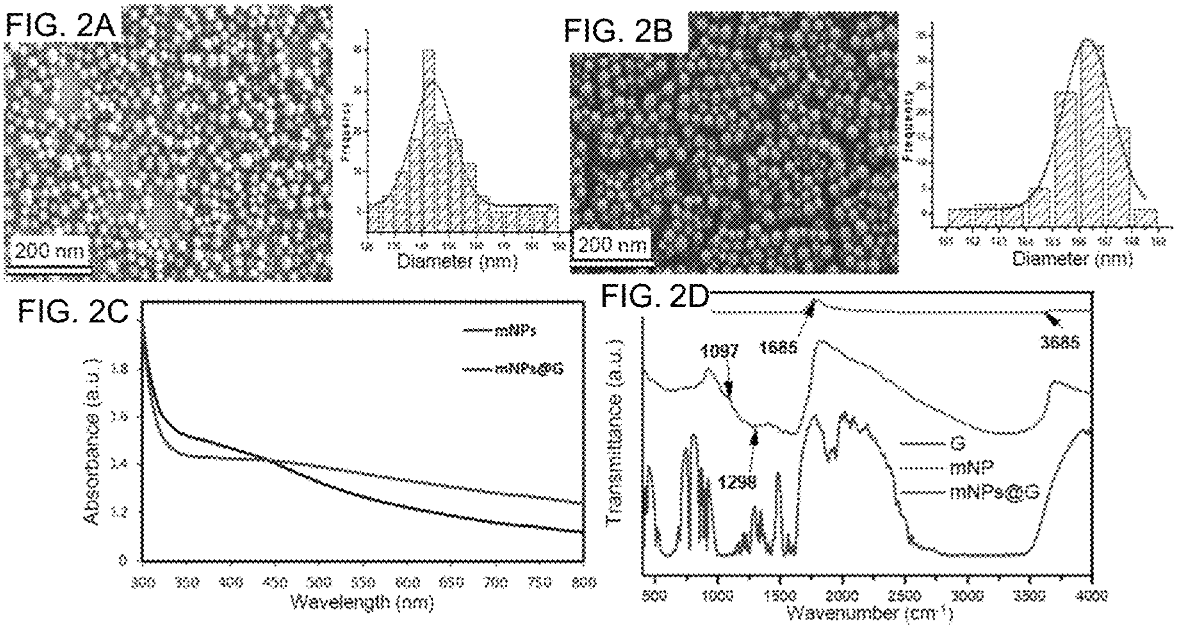
FIG. 2A is an SEM image and the corresponding size distribution histogram for mNP.
FIG. 2B is an SEM image and the corresponding size distribution histogram for mNP@G.
FIG. 2C is a plot of UV-Vis absorption of mNP and mNP@G.
FIG. 2D is an FTIR spectra of terminal amino glucose, mNP and mNP@G.

FIG. 2A is an SEM image and the corresponding size distribution histogram for mNP, FIG. 2B is an SEM image and the corresponding size distribution histogram for mNP@G, FIG. 2C is a plot of UV-Vis absorption of mNP (black/lower line at 700 nm) and mNP@G (red/upper line at 700 nm), FIG. 2D is an FTIR spectra of terminal amino glucose (bottom/black line), mNP (top/red line), and mNPs@G (middle/blue line). Comparing FIG. 2A and FIG. 2B, a slight increase in size, e.g., from 145 nm for mNPs to 166 nm for mNPs@G (i.e., with ~10 nm average glucose coating thickness), was observed after surface functionalization with amino sugar, indicating surface coverage by the glucose. FIG. 2C shows the optical absorption of aqueous solutions containing mNPs and mNP@G at the same concentration (0.1 g $L^{-1}$), recorded using UV-Vis-NIR spectroscopy. The spectra are similar, with the higher absorption of mNP@G in the visible range due to glucose coating. Surface functional groups of nanomaterials intended for biomedical application are crucial for their hydrophilicity and dispersibility in water and various biofluids. Thus, the chemical groups of melanin and the corresponding sugar-coated analog samples were determined using FTIR spectroscopy (FIG. 2D). The intense C═O stretches from aromatic rings and/or carboxyl groups of the mNPs that almost suppressed other peaks can be observed at 1685 $cm^{-1}$. The broad OH stretch of glucosamine alone can be visibly seen between 2700-3500 $cm^{-1}$. The FTIR of the mNPs@G displayed an overlap of $NH_2$/OH stretching around 3200-3500 $cm^{-1}$. The C—O and C—C vibrational band arising from Schiff's base reaction can be seen at 1097 $cm^{-1}$ and 1298 $cm^{-1}$ in the mNPs@G (FIG. 2D), indicating successful functionalization.

Cell Viability after mNP and mNP@G Uptake—Studies showed that: (1) non-cancerous or non-malignant cancer cells do not ingest mNPs, (2) studied malignant cancer cells massively absorb mNPs (macrophagic/phagocytic character), (3) this uptake is much stronger for the glucose-coated mNPs, (4) cell viability diminishes with increasing number of absorbed mNPs, and (5) lower glucose content in the cell nutrition dramatically reduces cell viability.

Figure 3A:
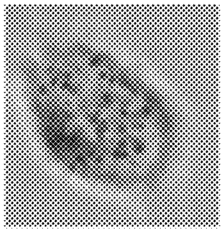
FIGS. 3A, 3B and 3C are optical microscope images of a VM-M3 cell
Figure 3B:
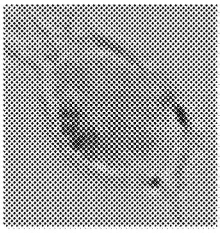
Figure 3C:
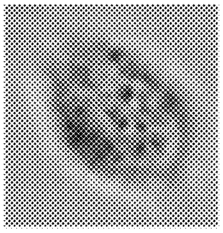
Figure 3D:
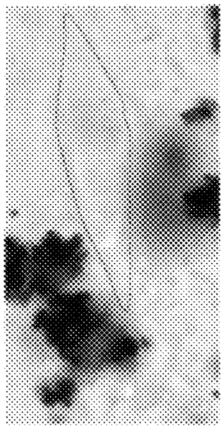
FIGS. 3D, 3E and 3F are optical microscope images of a VM-NM1 cell, taken at various focal plane depths: near the top cell surface (3A, 3D), middle of the cell (3B, 3E), and near the bottom cell surface (3C, 3F). Both cells are shown after 26 h incubation with mNPs. The common scalebar is 10 μm. The dashed lines in 3D and 3F outline the cell shape as in 3E.
Figure 3E:
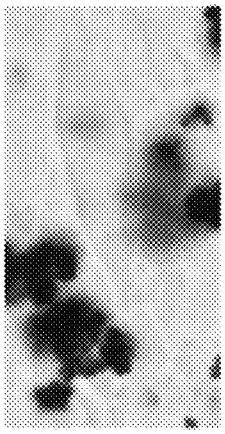
Figure 3F:
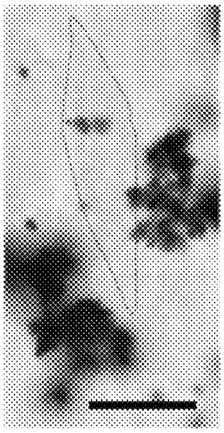

FIG. 3A-3F exemplifies the main observations (1) and (2) listed above. It shows optical microscope images of a VM-M3 cell (FIG. 3A, 3B, 3C) and a VM-NM1 cell (FIG. 3D, 3E, 3F), both exposed to approximately the same amount of mNPs (26 h incubation time) and taken with focal planes at increasing depth into a cell (from left to right). FIGS. 3A, 3B and 3C are optical microscope images of a VM-M3 cell and FIGS. 3D, 3E and 3F are optical microscope images of a VM-NM1 cell taken at changing focal plane depths. The images in FIGS. 3A and 3D were taken near the top cell surface. The images in FIGS. 3B and 3E were taken near the middle of the cell. The images in FIGS. 3C and 3F were taken near the near the bottom cell surface. Both cells are shown after 26 h incubation with mNPs. The common scale bar is 10 μm. The dashed line in FIGS. 3D and 3F outlines the cell shape as in FIG. 3E. This allows one to view cell interiors, and the nominal location of the absorbed nanoparticles. The malignant VM-M3 cell contains mNPs throughout its interior. In contrast, the non-malignant VM-NM1 cell has no mNPs in its interior; rather, these agglomerated in large clumps outside the cell. This confirms that only the malignant cells have phagocytic behavior. Similar tests show that healthy, non-cancerous cells also do not ingest mNPs.

Figure 4A:
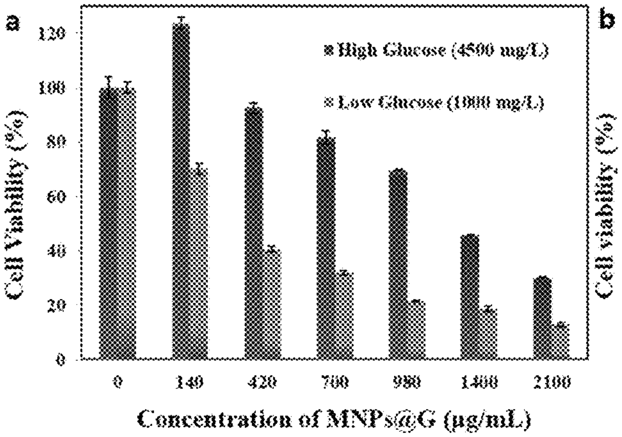
FIG. 4A shows A375 melanoma cell viability as a function of mNP@G concentration.
Figure 4B:
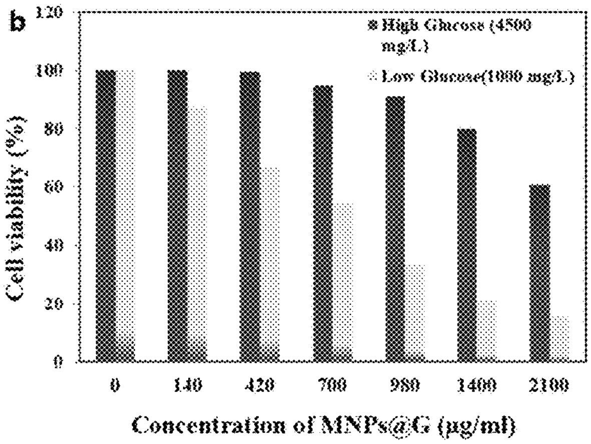
FIG. 4B shows HeLa cell viability as a function of mNP@G concentration and FIG. 4C shows data on type VM-M3 cancer cell viability for mNP vs. mNP@G loading.
Figure 4C:
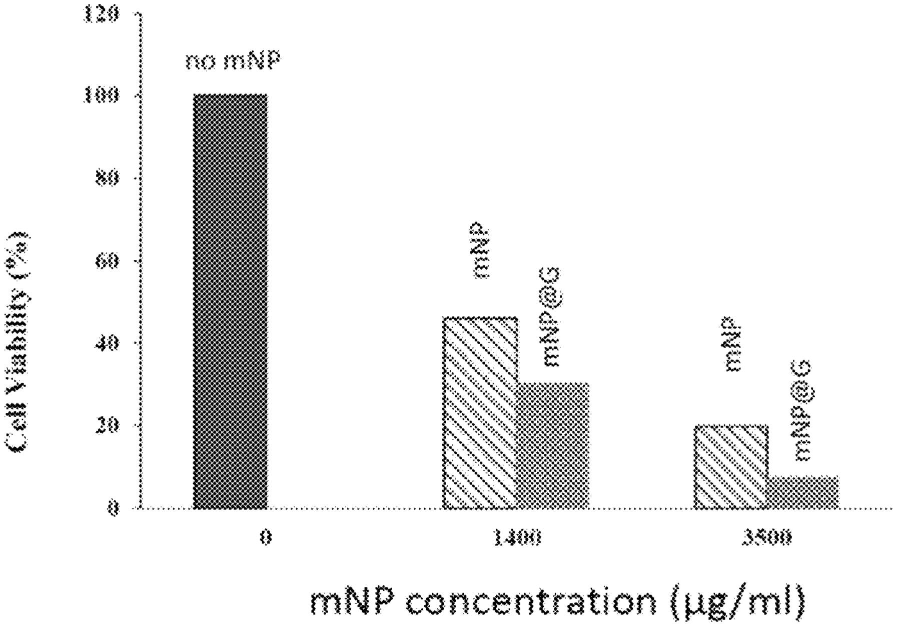

FIGS. 4A and 4B exemplify the main observations (3), (4) and (5) listed above. FIG. 4A (A375 melanoma cell) and FIG. 4B (HeLa cell) show viability according to CCK-8 assay as a function of mNP@G concentration after 62 h incubation in high glucose growth medium (4500 mg $L^{-1}$) and 15 h incubation in low glucose growth medium (1000 mg $L^{-1}$). FIG. 4C shows data on type VM-M3 cancer cell viability for mNP vs. mNP@G loading, without illumination. These data show evidence that, at the two representative mNP concentrations shown, cell viability decreases for mNP@G uptake vs. mNP uptake (i.e., glucose coating of mNPs reduces cell viability to a greater degree than uptake of mNPs without glucose coating).

FIG. 4A shows A375 cell viability versus concentration of mNP@G for two different glucose concentrations in the growth medium, and FIG. 4B shows similar effects for the HeLa cells that normally, in contrast to the melanoma cells, contain no melanin nanoparticles. An incubation time of 62 h was used for higher concentrations of glucose in the growth medium compared to lower concentrations. This is because cells absorb the molecular glucose from the growth medium before they begin absorbing the much larger, glucose-coated nanoparticles. Thus, the incubation time approximately scales with the glucose concentration in the growth medium. The higher cell viability at the same mNP concentration in high glucose concentration is consistent with the Warburg effect according to which cancer cells benefit from increased amounts of glucose in the medium.

The mechanism of the mNPs cytotoxicity may be due to the nanoscopic size of the mNPs, which increases surface area for molecular chemical reactions with the cell interior components. Note that melanin produced by melanocytes occurs in the form of microcrystals (average diameter D), much larger than mNPs (with average diameter d) and thus, for the same melanin volume, have much smaller surface area (approximately $(d/D)^2$). If melanin had some finite surface-based cytotoxic effect, it would be expected to be enhanced with mNPs. Biologically active melanin has indeed been reported to be cytotoxic.

Figures 5A, 5B, 5C, 5D, 5E, 5F, 5G, 5H:
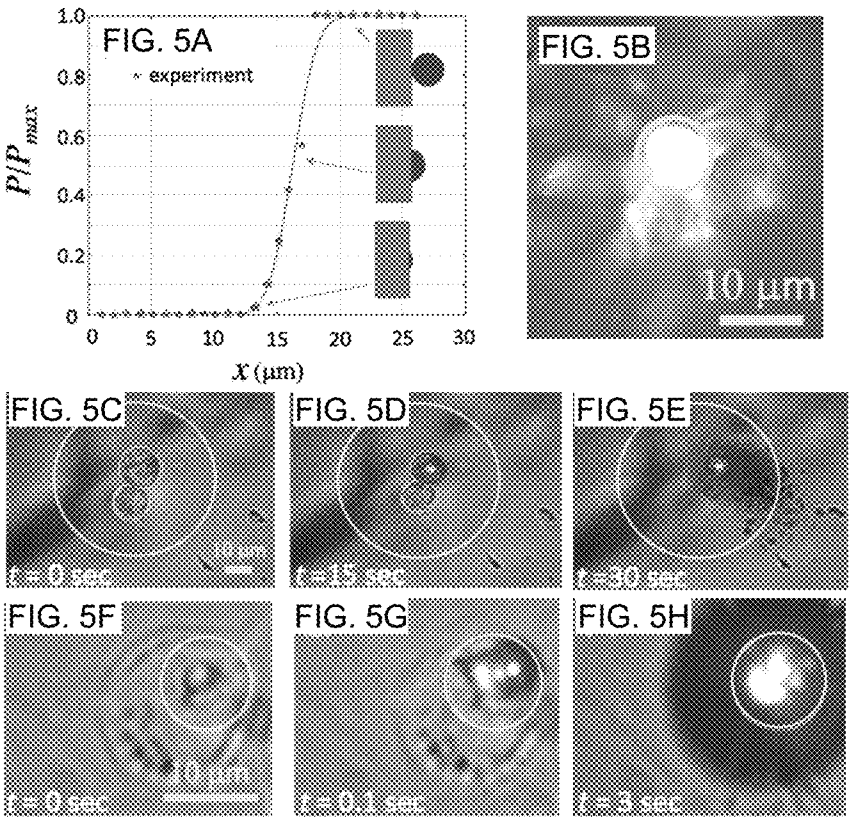
FIG. 5A is a plot of optical power versus position.
FIG. 5B is an optical image of the laser spot obtained by using the fluorescent card.
FIGS. 5C, 5D, 5E are each images of two VM-M3 cells moderately filled with mNPs at 10× magnification.
FIG. 5F, 5G, 5H are each images of a VM-M3 cell moderately filled with mNPs and laser radiation at 100× magnification.

Cell Viability after Exposure to Radiation—A laser system employing 532 nm wavelength light, can be coupled to the input port of a fluorescent microscope. The beam can be aligned and centered to the back aperture of an objective, and reflected light filtered with a dichroic mirror. The sample can be viewed and data recorded via Thorcam. The laser spot size on the sample can be determined by the knife edge technique. As the blade moves across a laser spot, the measured laser light power P varies from zero to $P_{max}$, and the shortest distance between these corresponding edge locations can be recorded. FIG. 5A shows a scaled plot of P vs. position x and the insets sketch approximate blade-beam locations at selected points, measured using the blade edge shading effect. FIG. 5B shows an optical image of the laser spot (with diameter D≈7 μm, marked by a yellow circle) on a fluorescent card, for a chosen magnification setup on the microscope.

FIGS. 5C-E show images of two VM-M3 cells moderately filled with mNPs, at various exposure times to laser light, at 10× magnification (light power density $\O_{inc}\approx 6\times 10^7$ W $m^{-2}$). FIGS. 5F-H show images of a VM-M3 cell moderately filled with mNPs, at various exposure times to laser radiation, at 100× magnification (power density $\O_{inc}\approx 1.4\times 10^9$ W $m^{-2}$). Yellow circles mark approximate beam diameter, which changes with magnification. Due to filtering, the laser spot is invisible, so its outline is marked with a ~50 μm diameter yellow circle. The power density, $\O_{inc}\approx 6\times 10^7$ W $m^{-2}$, is enough to initiate visible cell damage after 15 s of exposure, and catastrophic cell damage after 30 s. In a separate magnification and laser power, the effect on a different VM-M3 cell, moderately filled with mNPs, is shown in FIGS. 5F-5H. This laser spot (also marked with a yellow circle) has diameter~7 μm, and the corresponding power density is $\O_{inc}\approx 1.4\times 10^9$ W $m^{-2}$. The figure shows that the damage is now very localized, clearly starting at the clusters of mNPs, with damage obvious already after 0.1 s exposure, and complete catastrophic cell damage after only 3 s. The white spots visible inside the high laser intensity regions are due to photoluminescence of highly excited mNPs.

Figures 6A, 6B, 6C, 6D:
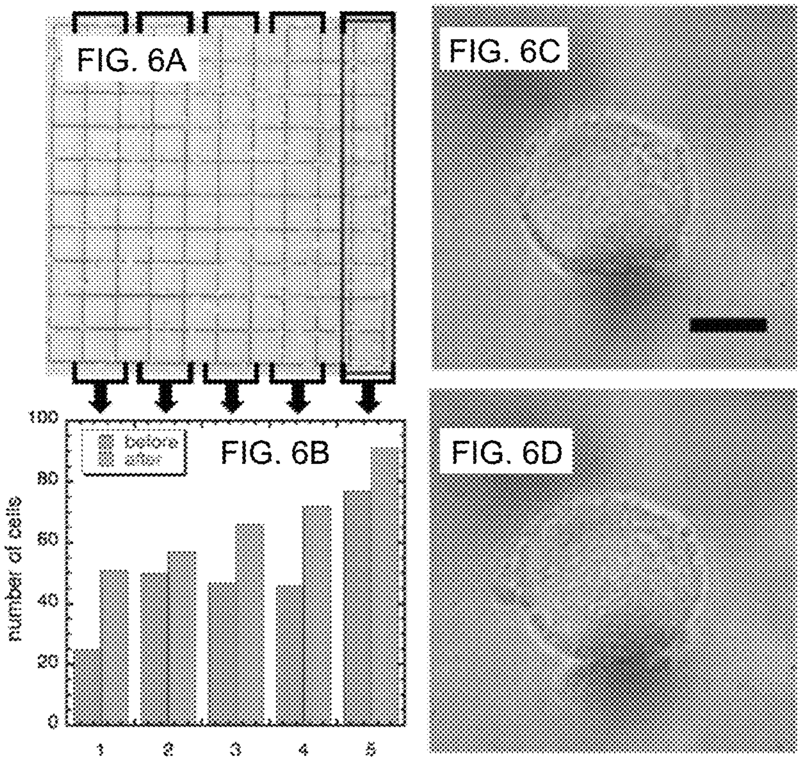
FIG. 6A shows a live/dead cell staining test.
FIG. 6B is a bar diagram of cell counts in boxes 1-5 of the test.
FIG. 6C is an image of an mNP-free, single VM-M3 cell before and FIG. 6D after laser exposure.

It was found that the level of radiation capable of catastrophically destroying mNP-filled VM-M3 cells, like in FIG. 5H, is safe for VM-M3 cells not sensitized with mNPs. mNP-unfilled cells grown on a microscopic slide that is marked with a 1 mm×1 mm grid enables one to track cells throughout an experiment. An optical microscope image of such a slide, shown FIG. 6A, was taken 24 h after exposure to laser light of cells in the box numbered 5 (solid-red outline). The cells experienced the same power density (and approximately the same exposure time) as the cell shown in FIG. 5H. The cells in the bracketed boxes 1~4 were not exposed to the laser. During the 24 h, the cells were incubated, and at the end, the Live/Dead Cell Staining Kit II (PromoKine) assay was applied, to visualize cell viability. FIG. 6A shows that the cells take up the Calcein-AM dye, resulting in green fluorescence, and are not permeable to the EthD-II dye, which would result in red fluorescence. Thus, all cells remain alive.

FIGS. 6A-6D show the effect of laser light on VM-M3 cells unfilled with mNPs. FIG. 6A shows live/dead cell staining test: all cells luminesce green and none luminesce red, indicating all are alive and growing. Only cells within the red-outlined, bracketed box have been exposed to the laser. FIG. 6B shows a bar diagram of cell counts in boxes 1-5, with red=before and blue=24 h after laser exposure of cells in box 5, all in growth medium. FIG. 6C shows an mNP-free, single VM-M3 cell before and FIG. 6D after laser exposure as described in the text. Scale bar 10 μm.

FIG. 6B shows a population bar diagram in the corresponding 5 boxes, where each box is represented by two bars: red bars before and blue bars after laser illumination of box 5. The red bars show that the initial cell distribution was roughly uniform in boxes 2-4 (with an average cell number per box~47), box 1 had ~25, and box 5, ~75 cells. After 24 h, the number of alive cells increased in all boxes (growing cells), including laser-exposed box 5. It is also clear that the overall distribution of cells on the grid changed, with the number of cells per box gradually increasing, e.g., to ~50 in box 1 and to ~90 in box 5. This effect results from a combination of natural cell population growth and temperature rise from laser heating of box 5, and the heat transfer away from this box. The resulting temperature profile during illumination would then be asymmetric, with a gradual temperature drop towards box 1, with cell growth reflecting this profile. One can demonstrate the lack of visible damage at the microscopic level via optical images of a single, mNP-unfilled MV-M3 cell before (FIG. 6C), and after (FIG. 6D) laser illumination, at the same level as applied in FIG. 6A. The radiation produces no visible change in the cell.

Figure 7:
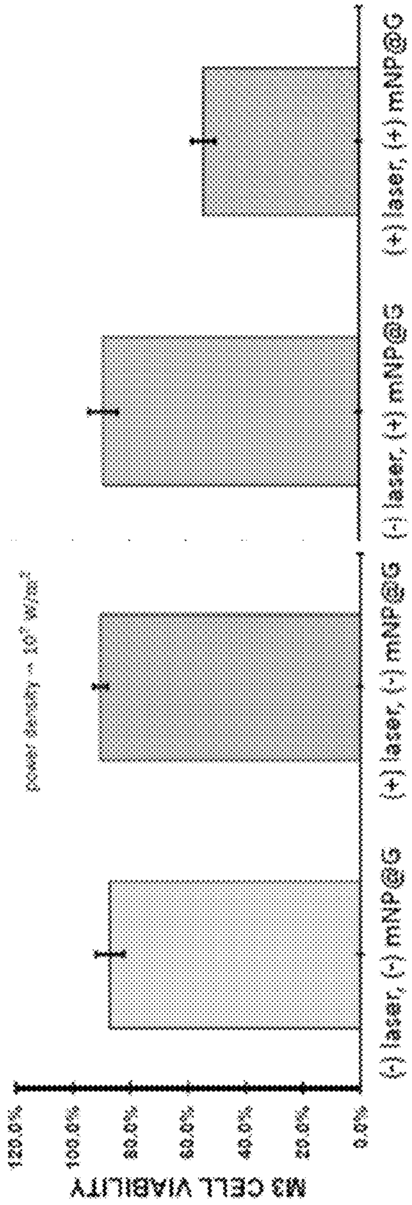
FIG. 7 shows VM-M3 cancer cell viability with/without laser illumination and with/without mNP@G loading.

FIG. 7 shows data on type VM-M3 cancer cell viability with/without 533 nm laser illumination and with/without mNP@G loading. These data show evidence that (a) light (at the representative wavelength, intensity and duration used) does not significantly affect cell viability, (b) mNP@G uptake (at the representative NP concentration and times used) does not significantly affect cell viability, and (c) light plus mNP@G uptake does significantly affect cell viability, reducing it by about half.

Figure 8:
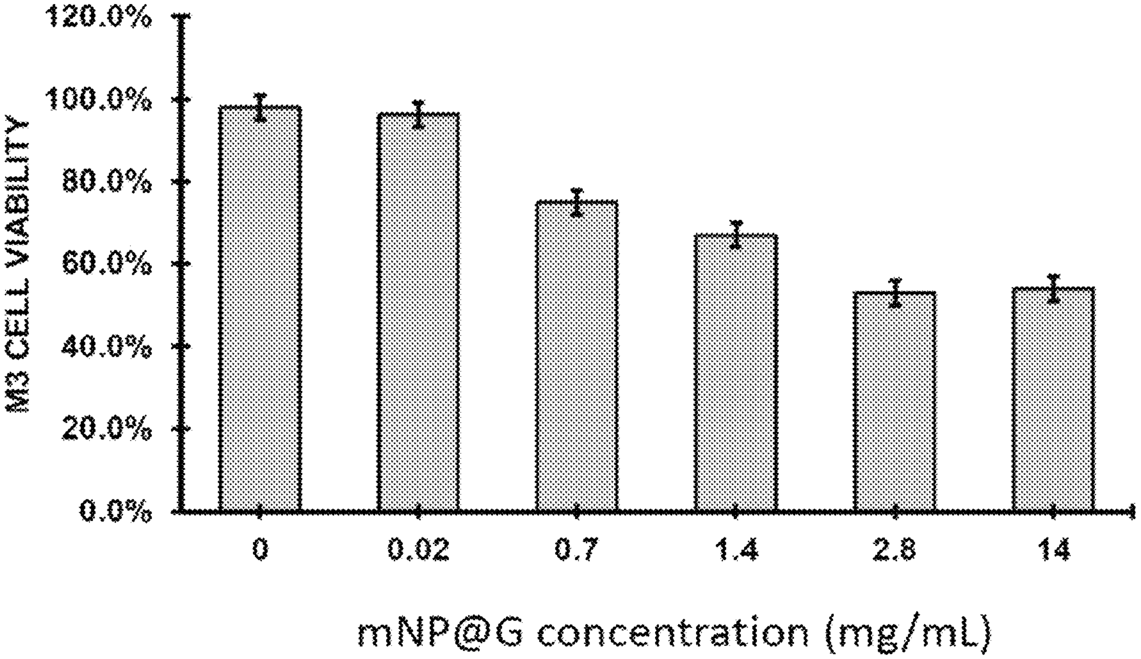
FIG. 8 shows VM-M3 cancer cell viability with no laser illumination and with mNP@G loading.

FIG. 8 shows data on type VM-M3 cancer cell viability with no laser illumination and with mNP@G loading. These data show evidence that at high mNP@G concentration, cell viability decreases, even in the absence of light. One can attribute this to over-eating/gorging, as well as to the strong uptake of mNPs coated with glucose (mNP@G) by cancer cells.

Based on the above results, one can conclude: (a) compared with the cytotoxicity of nanoparticles alone, laser-induced cell death requires much lower density of absorbed nanoparticles, (b) all cells filled with absorbing nanoparticles (e.g., mNPs) are destroyed by radiation, at sufficient power level—this would include melanoma cells, naturally filled with melanin microcrystals, and (c) there is a laser power range at which the nano-particle-filled cancer cells are violently destroyed, while the nanoparticle-free cells remain alive. This is key, since nanoparticle-filled cells do not have to be so violently destroyed to be killed, and so the applied laser power level can be strongly reduced. This lower power level will not damage nanoparticle-free cells.

Such a nanoparticle-based strategy could be used as a basis for or part of a cancer therapy (e.g., optochemotherapy), for example to target circulating tumor cells which mediate metastasis. In such a therapy, an intravenous injection could accomplish the first stage of the sugar-coated mNPs feeding into CTCs. This step could be enhanced by additional bio-engineered CTC targeting schemes. Next, in one possible scenario, one could expose the blood of a cancer patient to light externally, in a dialysis-like scheme. This would lead to a dramatic reduction in the CTC population, thus significantly reducing the effects of metastasis.

It has thus been observed that massive cellular uptake of melanin nanoparticles by metastatic cancer cells (macrophagic/phagocytic character) occurs which, at sufficiently high density, causes a cytotoxic effect. This effect is further enhanced by coating the nanoparticles with glucose, and simultaneous reduction of the glucose level in the growth medium. Nonionizing visible light at moderate power levels kills these metastatic cancer cells, at much lower mNP uptake levels. Cell death occurs in this case via hyperthermia-induced lysis, and this process is target-selective, as non-malignant cancer cells that could not ingest melanin nanoparticles remain unaffected, despite receiving identical optical energy levels and doses. This technique could enhance a future cancer metastasis-preventing therapy.

The rate of uptake of mNPs@G into metastatic cells is greater than the rate of uptake of un-sugar-coated mNPs. As such, the minimum energy (i.e., the product of light power and time) required to destroy cells sensitized with mNPs@G is less than that required by cells sensitized with uncoated mNPs, since the former will, on average, contain a higher number or density of NPs per cell.

Although various embodiments have been depicted and described in detail herein, it will be apparent to those skilled in the relevant art that various modifications, additions, substitutions, and the like can be made without departing from the spirit of the disclosure and these are therefore considered to be within the scope of the disclosure as defined in the claims which follow.

What is claimed:

1. A method for treating metastatic cancer cells, comprising:

coating melanin nanoparticles with sugar, wherein the coating is about 10 to 30 nm thick;

exposing metastatic cancer cells to the sugar-coated melanin nanoparticles causing nanoparticle uptake at a nanoparticle density to sensitize the cancer cells; and illuminating the sensitized cancer cells with a power level of nonionizing radiation sufficient to cause cell death.

2. The method of claim 1, wherein the sugar is glucose.

3. The method of claim 1, wherein the melanin nanoparticles have a diameter of between 50 and 350 nm.

4. The method of claim 1, wherein the metastatic cancer cells are VM-M3, A375 derived from melanoma, and HeLa.

5. The method of claim 1, wherein the nonionizing radiation is visible or IR light.

6. The method of claim 1, wherein exposing the metastatic cancer cells comprises injecting the sugar-coated melanin nanoparticles intravenously.

7. The method of claim 1, wherein illuminating the sensitized cancer cells comprises exposing the blood of a cancer patient to light externally, in a dialysis scheme.

8. The method of claim 1, wherein illuminating the sensitized cancer cells comprises exposing the blood of a cancer patient to light by direct radiation exposure of a near skin blood vessel.

9. The method of claim 8, wherein the illuminating is provided by a wrist-worn device by the patient.

* * * * *